United States Patent [19]

Liu et al.

[11] Patent Number: 4,940,687

[45] Date of Patent: Jul. 10, 1990

[54] CATALYST AND PROCESS FOR HYDROGENATION OF UNSATURATED HYDROCARBONS

[75] Inventors: Xin X. Liu; Bing Y. Zhao, both of Beijing, China; Herbert Riegel, Maplewood; Jo-Lung Chien, Cedar Grove, both of N.J.

[73] Assignees: Beijing Research Institute of Chemical Industry, Beijing, China; Lummus Crest, Inc., Bloomfield, N.J.

[21] Appl. No.: 229,211

[22] Filed: Aug. 5, 1988

Related U.S. Application Data

[60] Division of Ser. No. 858,546, Apr. 30, 1986, Pat. No. 4,762,956, which is a continuation of Ser. No. 484,626, Apr. 13, 1983, abandoned.

[51] Int. Cl.$^5$ .............................................. B01J 21/00
[52] U.S. Cl. .................................... 502/333; 502/325; 502/332
[58] Field of Search ........................ 502/333, 325, 332

[56] References Cited

U.S. PATENT DOCUMENTS 4,230,897 10/1980 Cosyns ................................ 502/333

FOREIGN PATENT DOCUMENTS 1249228 9/1967 Fed. Rep. of Germany ...... 502/333
2715094 10/1977 Fed. Rep. of Germany ...... 502/333
0157507 12/1979 Japan .................................. 502/333

*Primary Examiner*—William R. Dixon, Jr.
*Assistant Examiner*—James M. Hunter
*Attorney, Agent, or Firm*—Elliot M. Olstein; John G. Gilfillan, III; Raymond J. Lillie

[57] ABSTRACT

Dienes and/or acetylene impurities in an olefin feed; in particular a propylene feed, may be selectively hydrogenated in a single stage by use of a catalyst of palladium supported on alumina which is substantially crystalline alpha alumina, wherein the average pore radius is 200–2000 Å, with at least 80% of the pores having a pore radius within the range of 100 to 3000 Å. The surface acidity of the catalyst is generally from 0.002 to 0.05 millimole of pyridine absorbed per gram of catalyst. The active palladium surface area is from 20 to 200 m$^2$/g. The palladium is in the form of crystallines having an average size of at least 25 Å.

11 Claims, No Drawings

4,940,687

CATALYST AND PROCESS FOR HYDROGENATION OF UNSATURATED HYDROCARBONS

This application is a divisional of application Ser. No. 858,546, filed Apr. 30, 1986, now U.S. Pat. No. 4,762,956, which is a continuation of Ser. No. 484,626, filed Apr. 13, 1983, abandoned.

This invention relates to the selective hydrogenation of impurities in a feed containing hydrocarbons, and more particularly to the selective hydrogenation of acetylenic an/or diene impurities in a feed containing at least one mono-olefin.

In the petrochemical industry, there are produced streams which contain one or more mono-olefins, and which further contain, as impurities, acetylenic compounds and/or dienes. Thus, for example, propylene and/or butene cuts obtained from various pyrolysis processes, particularly pyrolysis in the presence of steam, contain, as impurities, acetylenic compounds and/or dienes, and in general, both acetylenic compounds and dienes. Among the acetylenic compounds, there may be mentioned acetylene, methylacetylene, and diacetylene, and among the dienes there may be mentioned propadiene, and 1,3-butadiene. Thus, for example, a propylene stream recovered from a steam pyrolysis process generally contains both methylacetylene and propadiene.

In the petrochemical industry, such a stream is subjected to a selective hydrogenation process in order to hydrogenate the acetylenic and/or diene impurities, while minimizing hydrogenation of the desired mono-olefin. In general, such a process is accomplished by a fixed bed catalytic hydrogenation, using a noble metal, such as palladium, supported on a suitable support as the selective hydrogenation catalyst. Thus, for example, such a process is described in U.S. Pat. No. 3,770,619.

The present invention is particularly directed to an improved method and catalyst for the selective hydrogenation of acetylenic and/or diene impurities in a feed which contains at least one mono-olefin.

In accordance with one aspect of the present invention, there is provided a new and improved catalyst which is particularly suitable for the selective hydrogenation of acetylenic and diene impurities which is comprised of a catalytic amount of palladium supported on an alumina support which is substantially crystalline alpha alumina wherein the catalyst has an average pore radius of from 200 to 2000Å, with at least 80% of the pores having a pore radius which falls within a range of from 100 to 3000Å.

In accordance with another aspect of the present invention, there is provided a process for the selective hydrogenation of acetylenic and/or diene impurities in a feed containing at least one mono-olefin wherein the feed is catalytically hydrogenated by use of a catalyst comprised of a catalytic amount of palladium supported on an alumina support which is substantially crystalline alpha-alumina, wherein the catalyst has an average pore radius of from 200 to 2000Å, with at least 80% of the pores having a pore radius which falls within the range of from 100 to 3000Å.

More particularly, the catalyst formulated in accordance with the present invention includes a catalytically effective amount of palladium, with the palladium content generally being at least 0.1, and preferably at least 0.2% by weight of the catalyst. In general, the palladium content of the catalyst need not exceed about 1%, and most generally need not exceed 0.5%, by weight of the catalyst.

As hereinabove noted, the average pore radius of the catalyst is from about 200 to 2000Å, preferably from 300 to 1500Å, and most preferably from 300 to 600Å. The pore size distribution is such that at least 80% of the pores have a radius within the range of from 100 to 3000Å, and preferably within the range of from 100 to 1000Å. Applicant has found that the combination of palladium supported on alpha alumina, with the noted characteristics of pore radius provides an improved catalyst for the selective hydrogenation of acetylenic and/or diene impurities in a feed which contains at least one mono-olefin.

The catalyst which is employed in the present invention generally has a surface area of no greater than 50 $m^2/g$ with the surface area generally being in the order of 3 to 30 $m^2/g$. The porosity of the catalyst is generally from 0.2 to 1.0 ml/g, (and preferably from 0.3 to 0.6 ml/g.) The surface acidity of the catalyst as measured by adsorption of pyridine at 120° C. and under atmospheric pressure is from 0.002 to 0.05 millimole of pyridine absorbed/g of catalyst.

The catalyst which is employed in the present invention generally has an active palladium surface area of from 20 to 200 $m^2/g$, and preferably from 40 to 120 $m^2g$, as measured by oxygen-hydrogen titration. In addition, the palladium is in the form of crystallites having an average size of at least 25Å and generally no greater than 100Å.

Applicant has found that the temperature at which the alpha alumina support is calcined, prior to addition of the palladium catalyst, has an influence on the average pore radius, which average pore radius has a direct effect on the catalytic activity and the ability of the catalyst to suppress formation of polymers. Applicant has found that the support is preferably calcined at a temperature generally exceeding 1400° C. in order to achieve a catalyst having the hereinabove described range of average pore radius.

The catalyst may be prepared by procedures generally known in the art, provided that the support is calcined at a temperature, as hereinabove described, so as to produce a catalyst having an average pore radius as hereinabove described.

The alumina support is preferably produced from a mixture of $\beta$-Al$_2$O$_3$. 3H$_2$O$\alpha$-Al$_2$O$_3$.H$_2$O and amorphous aluminum hydrozide, with the $\beta$-Al$_2$O$_3$.3H$_2$O being present in the mixture in an amount of from 5% to 35% by weight. As known in the art, the above mixture is prepared by neutralization of sodium aluminate by nitric acid at a suitable elevated temperature. The support may be shaped by a conventional procedure to produce either pellets, extrudates or granules, with the alumina support preferably being produced in a spherical shape. In general, the support is shaped into spherical pellets having a diameter in the order of from 1 to 8 mm. The shaped pellets are then calcined at a temperature of at least 1100° C., as hereinabove described, for a period of time which is generally in the order of from 1 to 8 hours.

After calcination, a solution of palladium chloride or palladium nitrate at a pH of from 3.3 to 6.0 is sprayed through a suitable atomizer onto a support which has been previously preheated, to a temperature in the order of from 20° to 50° C., followed by drying at a temperature in the order of from 60° to 120° C. By adjusting the pH as hereinabove described and carefully spraying the solution onto the support it is possible to provide a catalyst in which the palladium is present mainly in the regions of the support which are at least 160 microns below the geometric surface, and in some cases at least 500 microns below the geometric surface. The palladium supported on the alpha alumina support is then calcined at a temperature in the order of from 350° to 500° C., preferably not exceeding 500° C., to decompose the palladium chloride or palladium nitrate, with such calcining generally taking effect over a time period of from 4 to 10 hours. The catalyst is then reduced with a hydrogen-containing gas at a suitable pressure and at a temperature ranging from 25° to 150° C., preferably from 50° C. to 100° C., for a time period of from 3 to 10 hours to provide a palladium catalyst supported on an alumina support which is substantially crystalline alpha-alumina having the hereinabove average pore radius.

Although a preferred procedure for producing a selective hydrogenation catalyst in accordance with the invention has been particularly described, it is to be understood that such a catalyst may be produced by other procedures.

The catalyst produced in accordance with the present invention may be used for the selective hydrogenation of acetylenic and/or diene impurities in a feed containing a mono-olefin, and is particularly suitable for the purification of a propylene containing stream, which includes, as impurities, methylacetylene and propadiene. Thus, for example, in the manufacture of propylene by the cracking of hydrocarbons, acetylenic compounds are simultaneously produced, and although acetylenic compounds, and in particular acetylene, may be substantially completely removed from the propylene fraction by distillation, other impurities, and in particularly methylacetylene and propadiene, which have boiling points sufficiently close to that of propylene are difficult to separate from the propylene rich stream. The present invention is particularly suitable for the selective hydrogenation of methylacetylene and propadiene in such a propylene containing stream. It is to be understood, however, that the hereinabove described catalyst is also suitable for the selective hydrogenation of other acetylenic and/or diene impurities which are present in a feed which also contains a mono-olefin.

Although the catalyst prepared in accordance with the present invention is suitable for the selective hydrogenation of acetylenic and/or diene impurities in any one of a wide variety of catalytic hydrogenation systems, the catalyst permits effective hydrogenation of acetylenic and/or diene impurities in a single stage hydrogenation. The invention is further described with respect to the preferred single stage embodiment under adiabatic conditions.

In accordance with the preferred single stage hydrogenation, the feed is introduced as a liquid and may be partially or completely vaporized during the hydrogenation. In accordance with one embodiment the hydrogenation is effected in the liquid phase, with no more than 5% of the feed being vaporized during the hydrogenation. However, it may be advantageous to carry out the reaction with more than 5% of the feed being vaporized.

In accordance with the preferred embodiment, a feed to be selectively hydrogenated and the hydrogen-containing gas are introduced into the catalytic hydrogenation reactor at a temperature in the order of from 0° C. to 50° C., and the outlet temperature of the catalytic hydrogenation zone generally does not exceed 60° C. The catalytic hydrogenation zone is generally operated at a pressure in the order of from 14 to 35 Kg/cm$^2$.

Depending upon the level of acetylenic and diene impurities in the feed, the inlet temperature, and the allowable outlet temperature, it may be necessary to recycle a portion of the product to the reaction zone (the recycle is mixed with the feed and hydrogen prior to introduction into the reaction zone).

In general, the recycle ratio (based on fresh feed hydrocarbon) when used, does not exceed 5:1, preferably does not exceed 3:1; accordingly, the recycle ratio may range from 0:1 to 5:1.

The hydrogen is introduced into the reactor in an amount sufficient to provide for the required hydrogenation of the acetylenic and/or diene impurities, with an increase of the ration of hydrogen to impurities resulting in a decrease in the selectivity of the hydrogenation. In general, the hydrogen to impurity mole ratio is in the order of from 1 to 2.5 moles of hydrogen per mole of impurities, with the ratio, in most cases, being in the order of from 1.2 to 2.0 moles of hydrogen per mole of impurities, with particularly good results being obtained with a hydrogen to impurity mole ratio of from 1.2 to 1.6. The hydrogen may be introduced with a suitable diluent, such as methane.

The catalytic hydrogenation is generally effected at liquid hourly spaced velocities in the order of from 50 to 170 hours (preferably 90 to 165 hours$^{-1}$) with it being understood that there is obtained an increase in selectivity at higher liquid hourly space velocities. As should be apparent to those skilled in the art, at some point, an increase in the liquid hourly space velocity does not result in a corresponding increase in the selectivity. The selection of a particularly suitable liquid hourly space velocity and superficial mass flow rate should be apparent to those skilled in the art from the teachings herein.

In accordance with the preferred embodiment, wherein a propylene stream, containing methylacetylene and propadiene, as impurities, is subjected to selective hydrogenation in accordance with the present invention, such a propylene-containing stream generally contains from 0.5 to 5 mole percent, and in some cases even higher amounts, of such impurities. By proceeding in accordance with the invention, hydrogenation of such impurities is about 30% to 90% selective to propylene, as evidenced by a net propylene gain in the product, as compared to the feed. Generally, selectivities from 60% to 90% can be achieved.

In some cases, depending on the impurity content of the feed, as well as other factors, the product from the initial selective catalytic hydrogenation may be subjected to a second catalytic hydrogenation. It is to be understood, however, that the selective hydrogenation is preferably effected in a single stage. In the case where a second reactor or reaction zone is employed, such second reaction zone is generally operated at a pressure similar to the pressure of the first catalytic hydrogenation stage. The second reactor is generally operated at an inlet temperature in the order of from 30° to 50° C. and at an outlet temperature not in excess of about 60° C. The second stage is operated with a hydrogen to impurity mole ratio in the order of from 3 to 10 moles of hydrogen per mole of impurity, with the catalyst in the second stage preferably also being a palladium on alpha alumina catalyst of the type hereinabove described. When the reaction is carried out in the two stages, the first stage is preferably operated with less than 5% wt. vaporization of the feed.

The catalyst is preferably employed in the reactor of either the first or second stage as a trickle-flow fixed bed, although, as should be apparent to those skilled in the art, the catalyst may be employed in the reactor with other kinds of fixed bed.

The invention will be further described with respect to the following examples; however, the scope of the invention is not to be limited thereby:

EXAMPLE 1

Aluminum hydroxide powder containing 19% beta $Al_2O_3 \cdot 3H_2O$ was shaped by conventional means to spherical pellets having a diameter of 2 to 4 mm. The dry aluminum hydroxide pellets were calcined at a temperature of 1350° C. for a time period of 2.5 hours.

An aqueous solution of palladium chloride at a pH of 4.2 was sprayed onto the support through an atomizer and the resulting product was dried at a temperature of 80° C.

The supported catalyst was reduced by use of hydrogen gas at a temperature of 70°–90° C. and a pressure of 13 Kg/cm²(g) for a time period of 4–8 hours.

EXAMPLE 2

Aluminum hydroxide powder containing 19% beta $Al_2O_3 \cdot 3H_2O$ was shaped by conventional means to spherical pellets having a diameter of 2.0–3.0 mm. The dry aluminum hydroxide pellets were calcined at a temperature of 1150° C. for a time period of 4.0 hours.

An aqueous solution of palladium chloride at a pH of 3.6 was sprayed onto the support and the resulting product was dried at a temperature of 80° C.

The supported catalyst was reduced by use of hydrogen gas at a temperature of 70°–90° C. and at atmospheric pressure for a time period of 4–8 hours.

The catalyst produced in Examples 1 and 2 had the following properties:

|  | Example 1 | Example 2 |
| --- | --- | --- |
| Bulk Density, g/ml | 0.93 | 0.90 |
| Specfic Surface Area, m²/g | 4.0 | 15 |
| Pore volume, ml/g | 0.37 | 0.40 |
| Av. pore radius, Å | 1350 | 520 |
| Pd, Wt % | 0.39 | 0.27 |
| Surface Acidity, millimole pyridine/g catalyst | 0.017 | 0.03 |
| Pd Active Surface Area, m²/g | 40 | 115 |
| Pd Crystallites Avg. Size, Å | 103 | 36 |

EXAMPLE 3

The catalyst prepared in Example 1 is used in a single stage, in an adiabatic trickle-flow fixed bed for the selective hydrogenation of a propylene feed as follows:

TABLE 1

|  | A | B |
| --- | --- | --- |
| Inlet Temperature, °C. | 40 | 40 |
| Outlet Temperature, °C. | 60 | 57 |
| Pressure kg/cm²(g) | 25.2 | 23.5 |
| LHSV(v/v/hr) | 165 | 109 |
| H₂/(MA + PD)(molar ratio) | 1.60 | 1.9 |

TABLE 2

|  | A (Vol. %) | | B (Vol. %) | |
| --- | --- | --- | --- | --- |
|  | Feed | Effluent | Feed | Effluent |
| Propane | 3.14 | 3.54 | 2.26 | 3.55 |
| Propylene | 94.66 | 96.46 | 95.31 | 96.45 |
| Methyl Acetylene | 1.24 | <5 ppm | 0.79 | <5 ppm |
| Propadiene | 0.96 | <5 ppm | 0.64 | <5 ppm |
| C₄'s | trace | — | trace | — |
| Total | 100.00 | 100.00 | 100.00 | 100.00 |
| C₆+ | — | 0.025 wt % | — | 0.04 wt % |

EXAMPLE 4

The catalyst of Example 2 is used in a single stage, in an adiabatic trickle-flow fixed bed, for the selective hydrogenation of a propylene feed, as follows:

TABLE 3

| Inlet Temperature, °C. | 39 |
| --- | --- |
| Outlet Temperature, °C. | 58 |
| Pressure kg/cm²(g) | 22.5 |
| LHSV v/v/hr | 109 |
| H₂/(MA + PD) (molar ratio) | 1.32 |

TABLE 4

|  | Volume % | |
| --- | --- | --- |
|  | Feed | Effluent |
| Propane | 2.96 | 3.12 |
| Propylene | 94.89 | 96.88 |
| Methyl Acetylene | 1.14 | <5 ppm |
| Propadiene | 1.01 | 5 ppm |
| Total | 100.00 | 100.00 |
| C₆+ | — | 0.07 wt % |

The present invention is particularly advantageous in that by using the catalyst of the present invention for the selective hydrogenation of diene and acetylenic impurities in a stream containing a mono-olefin in particular propylene, such selective hydrogenation can be accomplished at higher liquid hourly space velocities, higher superficial volume velocities, and at higher inlet temperatures, with a reduced formation of polymeric byproduct. The reduction of formation of polymeric byproduct reduces the tendency of the catalyst to become clogged, which provides for a longer operating life. In addition, the catalyst is found to be more selective to the conversion of such impurities, and in particular, selective to conversion of methylacetylene and propadiene to propylene.

A particular advantage of the present invention is that dienes and/or acetylenes can be selectively hydrogenated in a feed containing mono-olefin; in particularly propylene, in a single stage.

By proceeding in accordance with the present invention, it is possible, for example, to selectively hydrogenate a propylene feed, including methyl acetylene and propadiene, in a single stage, to produce chemical grade propylene (50–1000 ppm of diene and acetylene) or polymer grade propylene (trace~50 ppm diene and acetylene).

Numerous modifications and variations of the present invention are possible in light of the above teachings, and therefore, within the scope of the appended claims, the invention may be practiced otherwise than as particularly described.

What is claimed:

1. A catalyst for selectively hydrogenating an impurity selected from the group consisting of acetylenic compounds, dienes, and mixtures thereof consisting essentially of:

palladium supported on an alumina support which is substantially crystalline alpha alumina, said support having been calcined at a temperature of at least 1150° C. and no greater than 1400° C., said palladium being present on said support in an amount effective to catalyze said selective hydrogenation, said catalyst having an average pore radius of from 200 to 2000Å, with at least 80% of the pores having a pore radius within the range of from 100 to 3000Å.

2. The catalyst of claim 1, wherein the support is prepared by calcining a mixture of $\beta$-$Al_2O_3$.$3H_2O$, $\alpha$-$Al_2O_3$.$H_2O$, and amorphous aluminum hydroxide, containing from 5% to 35%, by weight, of $\beta$-$Al_2O_3$.$3H_2O$, said calcining being effected at a temperature of at least 1150° C. and no greater than 1400° C.

3. The catalyst of claim 2 wherein the palladium is present in an amount of at least 0.1 percent, by weight.

4. The catalyst of claim 3, wherein the palladium content is no greater than 1 percent by weight.

5. The catalyst of claim 4, wherein the surface area is no greater than 50 m$^2$/g.

6. The catalyst of claim 5, wherein the surface area is from 3 to 30 m$^2$/g.

7. The catalyst of claim 6, wherein the porosity is from 0.2 to 1.0 ml/g.

8. The catalyst of claim 7, wherein the surface acidity is from 0.002 to 0.05 millimole pyridine/g catalyst.

9. The catalyst of claim 8, wherein the palladium is present mainly in the regions of the support which are at least 160 microns below the geometric surface.

10. The catalyst of claim 9, wherein the palladium is present mainly in the regions of the support which are at least 500 microns below the geometric surface.

11. A process for producing a catalyst comprising palladium supported on an alumina support which is substantially crystalline alpha alumina, comprising:

calcining an aluminum hydroxide powder support containing from 5% to 35%, by weight, of $\beta$-$Al_2O_3$.$3H_2O$ at a temperature of from 1150° C. to 1400° C.; depositing on the support an aqueous solution of a palladium salt selected from the group consisting of palladium chloride and palladium nitrate in an amount sufficient to provide from 0.1 to 1.0 percent, by weight, of palladium on the supported catalyst, said aqueous solution having a pH of from 3.3 to 6.0; and reducing the palladium salt on the support to provide palladium metal on the support.

* * * * *